United States Patent [19]

Nagao

[11] Patent Number: 4,645,649
[45] Date of Patent: Feb. 24, 1987

[54] APPARATUS FOR CURING RESIN FILMS COATED ON DENTAL RESIN PROSTHESIS

[75] Inventor: Kunihiko Nagao, Ichikawa, Japan

[73] Assignees: G-C Dental Industrial Corp.; Mitsubishi Rayon Co., Ltd., both of Tokyo, Japan

[21] Appl. No.: 345,479

[22] Filed: Feb. 3, 1982

[30] Foreign Application Priority Data

Apr. 27, 1981 [JP] Japan .................................. 56-59832

[51] Int. Cl.⁴ .......................... B01J 19/08; B01J 19/12
[52] U.S. Cl. .................................. 422/186.3; 422/186; 118/620; 34/4
[58] Field of Search .......................... 422/186, 186.30; 118/620; 34/4; 219/10.55 R

[56] References Cited

U.S. PATENT DOCUMENTS

| | | | |
|---|---|---|---|
| 3,440,385 | 4/1969 | Smith | 219/10.55 R |
| 3,676,058 | 7/1972 | Gray | 219/10.55 R |
| 3,790,801 | 2/1974 | Coleman | 422/186.30 |
| 3,872,349 | 3/1975 | Spero et al. | 422/186.30 |
| 3,994,073 | 11/1976 | Lackore | 34/4 |
| 4,141,060 | 2/1979 | Lackore et al. | 34/4 |

Primary Examiner—John F. Terapane
Assistant Examiner—Susan Wolffe
Attorney, Agent, or Firm—Oblon, Fisher, Spivak, McClelland & Maier

[57] ABSTRACT

An apparatus for curing resin films coated on dental prosthesis comprises in combination a casing 1, an activation energy-radiating lamp 4 disposed therein and adapted to give off the radiations of activation energy toward the prosthesis, a turntable 2 slidably disposed in the casing for detachment therefrom and a mechanism for lifting and lowering 5 the turntable by a knob arranged outside of the casing. A door is set up on the wall of the casing and the door has therethrough a viewing window.

2 Claims, 2 Drawing Figures

APPARATUS FOR CURING RESIN FILMS COATED ON DENTAL RESIN PROSTHESIS

BACKGROUND OF THE INVENTION

The present invention relates to an apparatus for curing resin films coated on dental resin prosthesis, which is designated to coat the prosthesis with a photopolymerizable resin liquid on their surface, and polymerize to cure the resultant resin films as by radiations of activation energy.

Conventional apparatus for preparing plastic prosthesis coated with an abrasion resistant resin have several disadvantages: they encounter difficulties in obtaining uniform coating and render it impossible to make use of the radiations of activation energy in their maximum efficiency, thus resulting in local fluctuations in the quality of cured resin films and failing to obtain a desired coating effect. This is because dental prosthesis have to be cured as placed on or suspended from a turntable kept at a fixed level in a casing or box.

SUMMARY OF THE INVENTION

An object of the present invention is to provide an apparatus and a process to eliminate the above-mentioned drawbacks and render curing smoother and make the operation easier. More particularly, it is a main object of the present invention to provide an apparatus for curing resin films coated on dental prosthesis, comprising in combination a casing 1 fitting a door on a wall of the casing, the door has therethrough a viewing window, an activation energy-radiating lamp 4 disposed therein and adapted to give off the radiations of activation energy toward the prosthesis, a turntable 2 slidably disposed in the casing in such a manner that it can slide in or out of the casing, and a mechanism for lifting and lowering 5 the turntable by a knob arranged outside of the casing.

According to the present invention, a build-up of heat generated from the activation energy radiatior per se and hence a lowering of the radiation intensity of activation energy are prevented by blowing an atmospheric wind around the radiator. A change in the shape of the prosthesis to be coated is also avoided by blowing a warm wind regulated to a given temperature into a curing chamber defined by disposing a quartz plate between the radiator and a turntable. Optionally, the prosthesis together with the turntable can be detached via a particular slidable mechanism from in the casing without touching them with the hand. Therefore, the prosthesis can be set while keepig a temperature suitable for the curing reaction of a coating material and the close contact of the coating material with the prosthesis. This assures time-saving, easy and uniform coating. The apparatus of the present invention also includes a turntable-lifting or -lowering mechanism by which, during curing the turntable, can visually be aligned from the outside of the casing with the zone, in which the radiation efficiency of activation energy reaches a maximum, in dependence of the shape of the prosthesis. In this connection, it is noted that the light intensity reaches a maximum at a position about 10 mm away from the radiating lamp in view of uniformity and other considerations, although it increases further at a position nearer to the lamp.

Thus, the apparatus of the present invention renders it possible to make use the most of the radiations of activation energy, and ensures time-saving and efficient curing reaction. In addition, the apparatus of the present invention always provides coatings of uniform quality.

BRIEF DESCRIPTION OF THE DRAWINGS

The above-mentioned and other objects and features of the present invention will become apparent from a reading of the following detailed description of preferred embodiment of the present invention with reference to the accompanying drawings, in which.

PREFERRED EMBODIMENTS OF THE INVENTION

Figure 1:
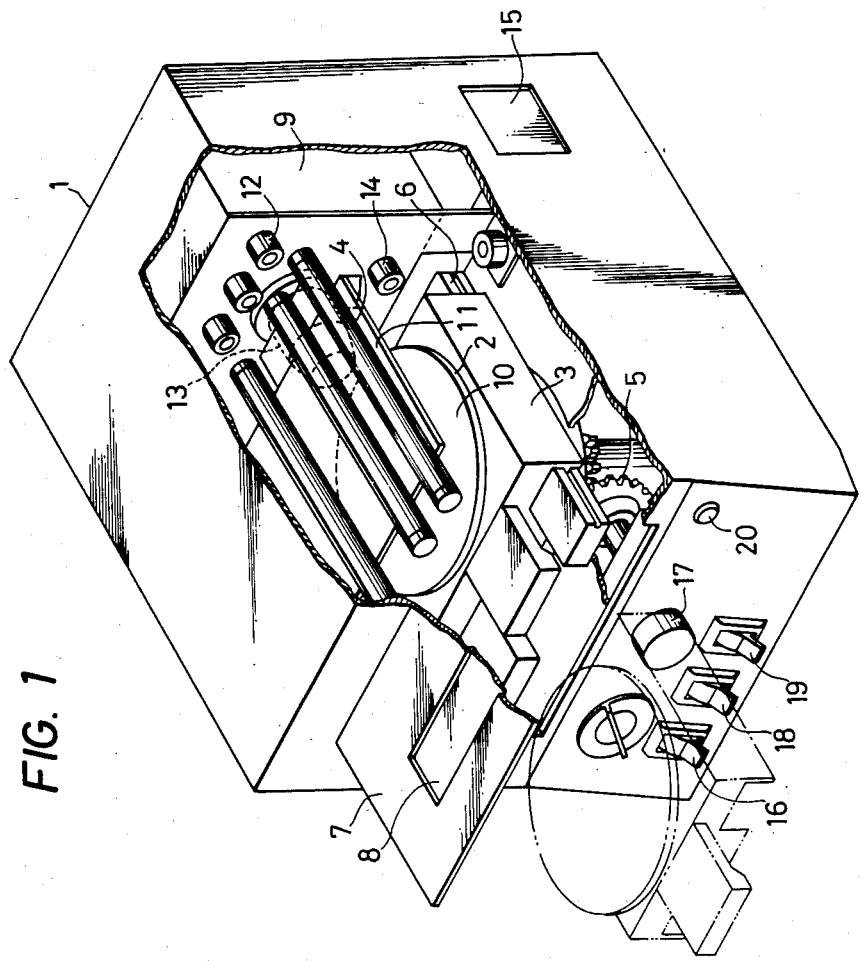
FIG. 1 is a perspective view, partially cut away, of the apparatus according to the present invention.
Figure 2:
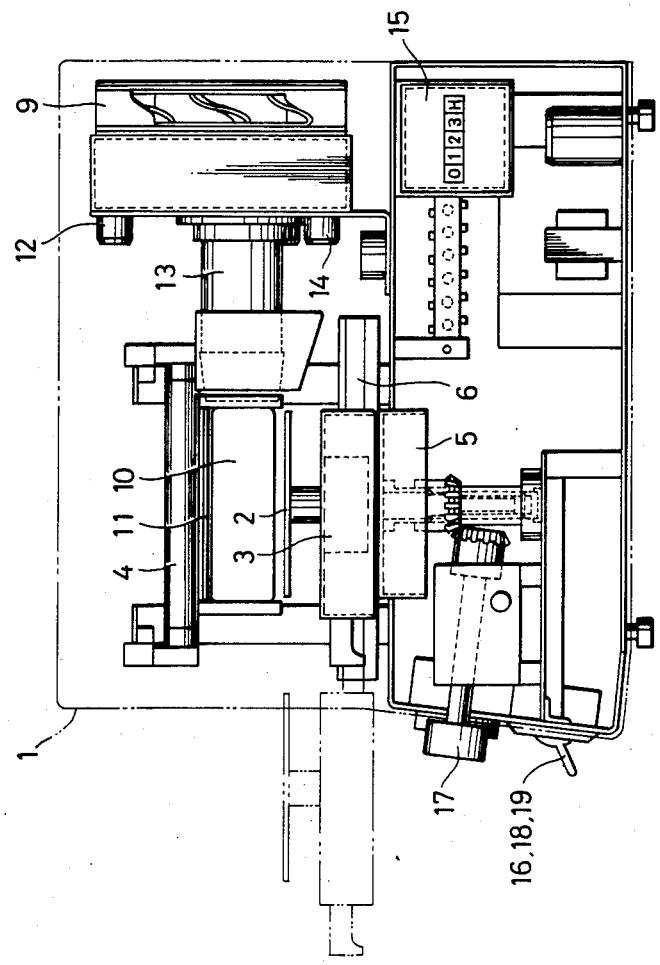
FIG. 2 is a sectional view of FIG. 1.

Referring to the drawings, the apparatus according to the present invention includes a casing 1 on a wall of which a door 7 is, fitted on a turntable 2 disposed therein for holding dental prosthesis, and a driving motor section 3 for rotating the turntable 2. The dental prosthesis held on the turntable 2 are exposed to the radiations of activation energy, while being rotated to receive uniformly thereover part of the radiations of activation energy reverberated from a reflector plate arranged in the casing. As mentioned above, the radiation intensity of activation energy is in inverse proportion to the second power of a distance between the dental prosthesis and an activation energy-radiating lamp 4. It is then required that the dental prosthesis be positioned as close to the lamp 4 as possible. By preference, the prosthesis are positioned about 10 mm away from the lamp 4 by vertically moving the turntable via a turntable-lifting and -lowering mechanism 5 by the manipulation of a knob 17 arranged outside of the casing, while visually monitoring it through a viewing window 8 formed in the door 7. This is because it is essentially important to set the dental prosthesis different in shape to the zone, in which the radiation efficiency of light energy reaches a maximum, during curing. It is noted that up and down movement of the turntable may be effected automatically.

Like furniture drawers, the turntable 2 having the prosthesis held thereon is longitudinally (or laterally) slid out of the casing 1 with the use of a horizontally movable sliding mechanism 6, while the height of the prosthesis is kept constant. Subsequent application of a coating liquid can be carried out with easiness and uniformity, since it is then feasible to coat the prosthesis in a stationary state without being subjected to any spacial limitations, while rotating the turntable.

With the activation energy-radiating lamp 4, the energy efficiency of which has a slight relation to the above-mentioned distance and varies largely dependent upon ambient temperatures, a rise of ambient temperatures entails a lowering of energy intensity, so that cooling of the lamp 4 is required. To this end, the lower portion of the lamp 4 is separated from a curing chamber 10 by a quartz partition 11 to cool the circumference of the lamp 4 with an atmospheric wind. This wind is obtained by the introduction of fresh air with a blowing fan 9 disposed in the casing 1. The fresh air thus introduced passes through inlets 12, 13 and 14 and is used to cool the lamp 4, warm the curing chamber 10 (with a heater disposed inside of the associated inlet 13) and cool the driving motor for the turntable 2, respectively.

The curing chamber 10 defined by the quartz partition 11 and turntable 2 has a temperature prevailing therein that is not too high to cause deformation of the prosthesis, and is designed to promote curing of the prosthesis by blowing thereonto a warm wind heated up to about 60° C. suitable for the curing reaction. The driving motor 3 for the turntable 2 is always cooled with an atmospheric wind introduced from the outside of the casing, and can be used for a longer period of time with no fear of superheating. This helps extend the motor's life.

The winds fed by the blowing fan 9 serve to cool the lamp 4 and control the temperature in the curing chamber 10 and, thereupon, are mixed together to cool the casing 1 in its entirety, leaving it through a discharge port. Since, in this way, use is effectively made of the radiations of activation energy, the curing reaction can be carried out for a shorter period of time and with efficiency, and bring about coatings of uniform quality.

Preferably, the casing according to the present invention should be formed of a material capable of resisting to the light and heat emanating from the lamp 4, such as a metal. Preferably, the casing has also an internal structure that includes a reflection mechanism to reflect and condense light.

The activation energy-radiating lamp 4 applied is not critical, and may be any types of lamps capable of giving off the radiations of activation energy. For instance, high- or low-pressure mercury lamps, or lamps capable of giving off ultraviolet rays or visible light.

One or more of radiating lamps 4 may also be used in combination. A lighting circuit for the lamp 4 may be of the a.c. type; however, it is more preferably of the d.c. type (i.e., the high frequency type), since further increases in energy efficiency is obtained.

Reference numerals 15, 16, 18, 19 and 20 not referred to in the foregoing stand for an integrator, a main switch, a driving motor switch, a lamp switch and an indicating lamp, respectively. For the simplicity of illustration, the operation and action of these members are not explained here, but would be selfevident to those skilled in the art.

The dental prosthesis to be used in the curing apparatus according to the invention typically includes dentures and dental plates formed of materials of resins or resin compositions such as methyl methacrylate polymers or copolymers polycarbonates and the like.

What is claimed is:

1. An apparatus for curing the coating of plastic prosthesis, comprising a casing, an ultraviolet lamp fixed in place within said casing to emit ultraviolet light towards dental prosthesis, a turntable slidable in or out of said casing, which is provided with an ascending and descending mechanism operable by a button outside said casing, a door attached to said casing provided with a viewing window, a curing chamber defined within said casing by a quartz partition plate arranged between said lamp and said turntable, a heater built in an air discharge port to feed directly into said curing chamber warm air regulated to a given temperature, other air discharge port disposed in such a manner that cooling air is supplied directly to said lamp and a driving motor for said turntable, and a single blowing fan designed to blow air to both said air discharge ports.

2. The apparatus as recited in claim 1, in which a reflecting plate is disposed on inner surface of the wall of said casing.

* * * * *